(12) United States Patent
Ouchi (10) Patent No.: US 10,331,010 B2
(45) Date of Patent: Jun. 25, 2019

(54) TERAHERTZ-WAVE GENERATING ELEMENT TERAHERTZ-WAVE DETECTING ELEMENT AND TERAHERTZ TIME-DOMAIN SPECTROSCOPY DEVICE

(71) Applicant: CANON KABUSHIKI KAISHA, Tokyo (JP)

(72) Inventor: Toshihiko Ouchi, Machida (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 37 days.

(21) Appl. No.: 15/353,211

(22) Filed: Nov. 16, 2016

(65) Prior Publication Data

US 2017/0059963 A1    Mar. 2, 2017

Related U.S. Application Data

(63) Continuation of application No. 14/830,511, filed on Aug. 19, 2015, which is a continuation of application
(Continued)

(30) Foreign Application Priority Data

Mar. 4, 2010   (JP) ................................ 2010-048323
Feb. 4, 2011   (JP) ................................ 2011-022706

(51) Int. Cl.
  *G02F 1/35*    (2006.01)
  *G01J 3/42*    (2006.01)
(Continued)

(52) U.S. Cl.
  CPC .......... *G02F 1/3544* (2013.01); *G01J 3/0216* (2013.01); *G01J 3/42* (2013.01);
(Continued)

(58) Field of Classification Search
  CPC .................................................. G02F 1/3544
  See application file for complete search history.

(56) References Cited

U.S. PATENT DOCUMENTS 3,584,230 A    6/1971   Tien
8,390,922 B1*  3/2013   Baehr-Jones ......... G02F 1/3534
                                                   359/332
(Continued)

FOREIGN PATENT DOCUMENTS

CN    101221296 A    7/2008
JP    H02-221941 A   9/1990
(Continued)

OTHER PUBLICATIONS

Tetsuya Kinoshita et al., "C-7 Efficient Electro-Optic Sampling Detection of THz Wave With Cherenkov-Type Phase Matching," Winnewwisser, et al, Appl. Phts. Lett. 70, 3069 (1997).
(Continued)

*Primary Examiner* — Edwin C Gunberg
(74) *Attorney, Agent, or Firm* — Canon U.S.A., Inc. IP Division (57) ABSTRACT

A terahertz-wave generating element includes a waveguide including an electro-optic crystal; an optical coupling member that extracts a terahertz wave, which is generated from the electro-optic crystal as a result of light propagating through the waveguide, to a space; and at least two electrodes that cause a first-order electro-optic effect in the electro-optic crystal by applying an electric field to the waveguide so as to change a propagation state of the light propagating through the waveguide. A crystal axis of the electro-optic crystal of the waveguide is set such that the terahertz wave generated by a second-order nonlinear optical process and the light propagating through the waveguide are phase-matched.

41 Claims, 8 Drawing Sheets

Related U.S. Application Data

No. 13/581,434, filed as application No. PCT/JP2011/054674 on Feb. 23, 2011, now Pat. No. 9,152,009.

(51) Int. Cl.

| | | |
|---|---|---|
| *G01J 3/02* | (2006.01) | |
| *G01N 21/3586* | (2014.01) | |
| *G01N 21/47* | (2006.01) | |
| *G02F 1/035* | (2006.01) | |
| *G02F 1/39* | (2006.01) | |
| *G02F 1/377* | (2006.01) | |
| *G02F 1/37* | (2006.01) | |

(52) U.S. Cl.
CPC ..... *G01N 21/3586* (2013.01); *G01N 21/4795* (2013.01); *G02F 1/0356* (2013.01); *G02F 1/377* (2013.01); *G02F 1/395* (2013.01); *G01N 2201/06113* (2013.01); *G02F 2001/3546* (2013.01); *G02F 2001/374* (2013.01); *G02F 2203/13* (2013.01)

(56) References Cited

U.S. PATENT DOCUMENTS

| | | | | |
|---|---|---|---|---|
| 9,152,009 | B2* | 10/2015 | Ouchi | G01N 21/3586 |
| 2008/0265165 | A1* | 10/2008 | Yeh | G02F 1/35 |
| | | | | 250/341.1 |
| 2009/0283680 | A1 | 11/2009 | Logan, Jr. | |

FOREIGN PATENT DOCUMENTS

| | | |
|---|---|---|
| JP | 2003505130 A | 2/2003 |
| JP | 2003-324226 A | 11/2003 |
| JP | 2005-031574 A | 2/2005 |
| JP | 2006171624 A | 6/2006 |
| JP | 2007163579 A | 6/2007 |
| JP | 2008-020268 A | 1/2008 |
| JP | 2008164594 A | 7/2008 |
| JP | 2009-175127 A | 8/2009 |
| JP | 2010-204488 A | 9/2010 |
| JP | 2011203718 A | 10/2011 |
| WO | 2008/143737 A2 | 11/2008 |

OTHER PUBLICATIONS

Janos Hebling et al., "Generation of High-Power Terahertz Pulses by Tilted-Pulse-Front Excitation and Their Application Possibilities," J. Opt. Soc. Am. B, vol. 25, No. 7, pp. B6-B19, Jul. 2008.

Koji Suizu, et al., "Extremely Frequency-Widened Terahertz Wave Generation Using Cherekov-Type Radiation," Optics Express, vol. 17, No. 8, pp. 6676-6681, Apr. 13, 2009.

Toshiaki Suhara, et al.; "Theoretical Analysis of Laterally Emitting Terahertz-Wave Generation by Difference-Frequency Generation in Channel Waveguides;" IEEE Journal of Quantum Electronics, vol. 39, No. 1, Jan. 2003; pp. 166-171, XP11065343.

M. Theuer et al; "Efficient Generation of Cherenkov-Type Terahertz Radiation from a Lithium Niobate Crystal with a Silicon Prism Output Coupler;" Applied Physics Letters; vol. 88; Feb. 17, 2006; pp. 071122-1 to 071122-3.

* cited by examiner

TERAHERTZ-WAVE GENERATING ELEMENT TERAHERTZ-WAVE DETECTING ELEMENT AND TERAHERTZ TIME-DOMAIN SPECTROSCOPY DEVICE

CROSS-REFERENCE TO RELATED APPLICATION

This application is a Continuation of co-pending U.S. patent application Ser. No. 14/830,511 filed Aug. 19, 2015 which is a Continuation of U.S. patent application Ser. No. 13/581,434 filed Aug. 27, 2012, now a U.S. Pat. No. 9,152,009, issued on Oct. 6, 2015; which was a National Phase application of International Application PCT/JP2011/054674, filed Feb. 23, 2011; which claims the benefit of Japanese Patent Applications No. 2010-048323, filed Mar. 4, 2010, and No. 2011-022706, filed Feb. 4, 2011, which are hereby incorporated by reference herein in their entirety.

TECHNICAL FIELD

The present invention relates to terahertz-wave generating elements that generate terahertz waves including electromagnetic wave components in a frequency range from a millimeter wave band to a terahertz wave band (30 GHz to 30 THz), terahertz-wave detecting elements that detect terahertz waves, and terahertz time-domain spectroscopy devices that use at least one of the above. In particular, the present invention relates to a generating element that includes an electro-optic crystal for generating or detecting an electromagnetic wave including a Fourier component in the aforementioned frequency range by laser light irradiation, and to a tomography device that uses the aforementioned generating element to perform terahertz time-domain spectroscopy (THz-TDS).

BACKGROUND ART

In recent years, non-destructive sensing techniques using terahertz waves have been developed. As an application field of electromagnetic waves in this frequency band, there is a technique of performing imaging by using safe fluoroscopic devices in place of X-ray devices. Furthermore, other techniques that have been developed include a spectroscopic technique for checking the physical properties, such as a molecularly bonded state, by determining the absorption spectrum or the complex permittivity of the inside of a material, a measurement technique for checking the physical properties, such as carrier concentration, mobility, or conductivity, and a biomolecular analyzing technique. As a method of generating a terahertz wave, a method that uses a nonlinear optic crystal has been widely used. Typical examples of nonlinear optic crystals include LiNbOx (also known as LN), LiTaOx, NbTaOx, KTP, DAST, ZnTe, GaSe, GaP, and CdTe. A second-order nonlinear phenomenon is used for generating a terahertz wave. Known methods for generating terahertz waves include a method of generating a difference in frequencies by inputting two beams of laser light having different frequencies, a method of generating a monochromatic terahertz pulse by an optical parametric process, and a method of generating a terahertz pulse by optical rectification using femtosecond pulse laser light.

Figure 8:
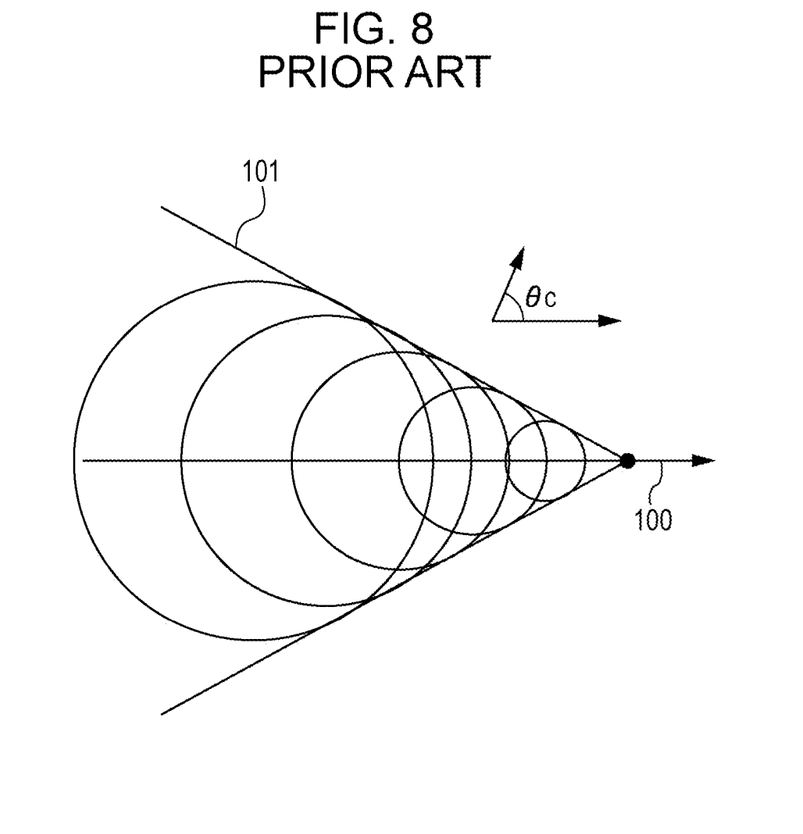
FIG. 8 is a conceptual diagram of electro-optic Cerenkov radiation.

As a process for generating a terahertz wave from a nonlinear optic crystal in this manner, electro-optic Cerenkov radiation has recently been drawing attention. As shown in FIG. 8, this is a phenomenon in which, when the propagation group velocity of laser light 100 serving as an excitation source is higher than the propagation phase velocity of a generated terahertz wave, a terahertz wave 101 is released in the form of a cone, like a shock wave. Based on a refractive-index ratio between the light and the terahertz wave within a medium (nonlinear optic crystal), a radiation angle θc is determined from the following equation.

$$\cos \theta c = v_{THz}/vg = ng/n_{THz}$$

In this case, vg and ng respectively denote the group velocity and the group refractive index of excitation light, and $v_{THz}$ and $n_{THz}$ respectively denote the phase velocity and the refractive index of a terahertz wave. There has been a report with regard to using this Cerenkov radiation phenomenon to make wavefront-tilted femtosecond laser light enter LN so as to generate a high-intensity terahertz pulse by optical rectification (see NPL 1). Furthermore, there has also been a report with regard to generating a monochromatic terahertz wave by a DFG method using a slab waveguide having a thickness that is sufficiently smaller than the wavelength of a generated terahertz wave so as to eliminate the need for a wavefront tilt (see PTL 1 and NPL 2).

Because terahertz waves are generated by traveling wave excitation in the examples in these literatures, the terahertz waves generated from different wave sources intensify each other by being phase-matched in the radiation direction, thus increasing the extraction efficiency. This radiation method is characterized in that a high-intensity terahertz wave can be generated since relatively high efficiency can be achieved when a nonlinear optic crystal is used, and that the terahertz wave band can be broadened by selecting a high-frequency side for the absorption of a terahertz region by phonon resonance, which is unique to crystals. With these techniques, the terahertz generation range can be broadened as compared with terahertz generation using photoconductors, the pulse width can be reduced in the case of terahertz pulse generation using optical rectification, and the device performance can be enhanced when the techniques are applied to, for example, terahertz time-domain spectroscopy devices.

CITATION LIST

Patent Literature

PTL 1 Japanese Patent Laid-Open No. 2010-204488

Non Patent Literature

NPL 1 J. Opt. Soc. Am. B, vol. 25, pp. B6-B19, 2008
NPL 2 Opt. Express, vol. 17, pp. 6676-6681, 2009

SUMMARY OF INVENTION

However, in the methods discussed in NPL 1 and NPL 2, light is simply passively irradiated onto the nonlinear optic crystal, and an adjusting unit for performing modulation on the generated terahertz wave is not included. Therefore, an external adjusting unit is required for adjusting the intensity of the terahertz wave. For example, although a rotatable light chopper is generally used when performing synchronous detection, since such a light chopper is of a mechnical type, the modulation speed is several kHz at most, and about 50% of the excitation light is cut. Therefore, the total terahertz generation efficiency is reduced, possibly becoming a hindrance to achieving an improved S/N ratio of the terahertz time-domain spectroscopy device.

A terahertz-wave generating element according to an aspect of the present invention includes a waveguide including an electro-optic crystal; an optical coupling member that extracts a terahertz wave, which is generated from the electro-optic crystal as a result of light propagating through the waveguide, to a space; and at least two electrodes that cause a first-order electro-optic effect in the electro-optic crystal by applying an electric field to the waveguide so as to change a propagation state of the light propagating through the waveguide. A crystal axis of the electro-optic crystal of the waveguide is set such that the terahertz wave generated by a second-order nonlinear optical process and the light propagating through the waveguide are phase-matched.

In the terahertz-wave generating element according to the aspect of the present invention, since the electrodes serving as an electrical modulating unit apply an electric field to the waveguide including the electro-optic crystal so as to change the propagation state of the propagating light by a first-order electro-optic effect, the generated terahertz wave can be modulated at a relatively high speed. Other aspects of the present invention will become apparent from embodiments to be described below.

DESCRIPTION OF EMBODIMENTS

A terahertz-wave generating element including an electro-optic crystal according to the present invention changes the propagation state of light propagating through a waveguide by causing a change in the refractive index in accordance with a first-order electro-optic effect of an electro-optic crystal by applying an electric field to the waveguide, thereby modulating a terahertz wave generated from the propagating light. In order to ensure the generation of a terahertz wave, the crystal axis of the electro-optic crystal is set such that a terahertz wave generated by a second-order nonlinear process and the propagating light can be phase-matched. Based on this concept, the terahertz-wave generating element according to the present invention has the above-described basic configuration. In this configuration, in order to efficiently modulate the terahertz wave by the electric-field application by the electrodes, the crystal axis of the electro-optic crystal is preferably set such that the first-order electro-optic effect of the electro-optic crystal caused by the electric-field application is at maximum. Furthermore, with the same configuration, the terahertz wave can be detected by a reverse process. The electro-optic crystal used here for the first-order electro-optic effect has second-order nonlinearity, and a generally practical electro-optic crystal is substantially equivalent to a nonlinear optic crystal having second-order nonlinearity.

Embodiments and a practical example will be described below with reference to the drawings.

First Embodiment

Figure 1A:
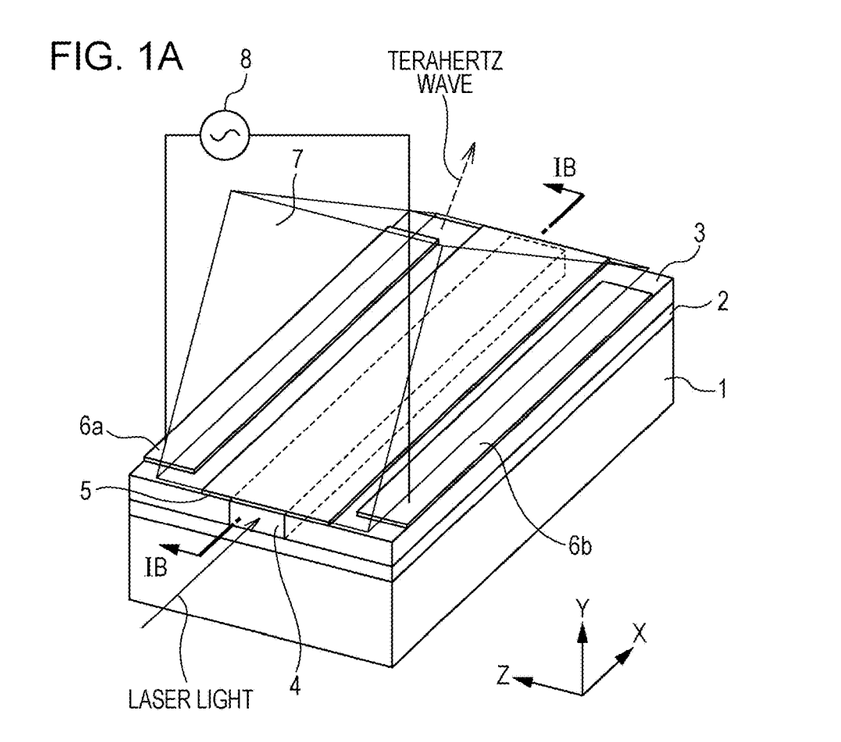
FIG. 1A is a perspective view of a terahertz-wave generating element according to a first embodiment of the present invention.
Figure 1B:
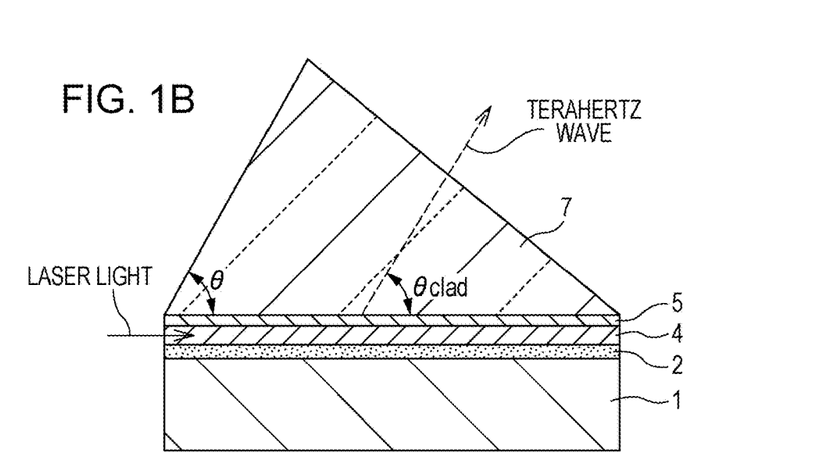
FIG. 1B is a cross-sectional view of the terahertz-wave generating element according to the first embodiment of the present invention.

A terahertz-wave generating element that uses a LN crystal according to a first embodiment of the present invention will now be described with reference to FIGS. 1A and 1B. FIG. 1A is a perspective view of the terahertz-wave generating element, and FIG. 1B is a cross-sectional view taken along line IB-IB in a waveguide of the terahertz-wave generating element. A LN substrate 1 is composed of Y-cut lithium niobate, and the LN crystal has an X axis corresponding to a propagating direction of laser light, a Y axis, and a Z axis corresponding to a direction orthogonal to the propagating direction (X axis) (see coordinate axes shown in FIG. 1A). With such a configuration, electro-optic Cerenkov radiation, which is a second-order nonlinear phenomenon, can be efficiently generated, and an electric field for causing a change in refractive index by a first-order electro-optic effect (Pockels effect) can be readily applied. In detail, a crystal axis of the LN crystal serving as an electro-optic crystal of the waveguide, to be described later, is set so as to efficiently cause a change in the refractive index by maximizing the first-order electro-optic effect by electric-field application, to be described later, and to efficiently change the propagation state of propagating light. In addition, the crystal axis is also set such that a terahertz wave generated by a second-order nonlinear process and the propagating light can be phase-matched. Specifically, the crystal axis is set such that a phase-matching condition is satisfied between wave number vectors of light waves (i.e., the terahertz wave and the propagating light) involved with the second-order nonlinear process.

On the LN substrate 1, an adhesive 2, a waveguide layer 4 formed of a MgO-doped LN crystal layer, and a low-refractive-index buffer layer 5 form a waveguide that propagates input laser light by total internal reflection. Specifically, the refractive indices of the adhesive 2 and the low-refractive-index buffer layer 5 are set to be lower than that of the waveguide layer 4. The adhesive 2 is required if the waveguide is to be fabricated by bonding the components together, but is not necessarily required if a doped layer is to be formed by diffusion or the like. Even in this case, the function of a waveguide is still achieved since the MgO-doped LN layer has a refractive index that is higher than that of the LN substrate 1. The structure of the waveguide can be formed by, for example, varying the refractive indices between the waveguide layer 4 and a surrounding region 3 by increasing the refractive index of the waveguide layer 4 by Ti diffusion or by forming the waveguide layer 4 into a ridge pattern by etching and embedding resin or the like into the surrounding region 3. Although the waveguide structure is also formed in the lateral direction (Z-axis direction), as in the waveguide shown in the drawings, so as to increase the light confinement properties, a slab waveguide in which the waveguide region extends uniformly in the lateral direction so as to include the region 3 but not a confinement region is also permissible. An optical coupling member 7 that extracts the generated terahertz wave to the outside and a pair of electrodes 6a and 6b (sometimes collectively referred to as "electrodes 6" hereinafter) for applying voltage from a power source 8 to the waveguide are provided on the waveguide including the waveguide layer 4. The optical coupling member 7 may be, for example, a prism, a diffraction grating, or a photonic crystal (in this case, a prism is shown in the drawings). The electrodes 6a and 6b extend in the X-axis direction and are disposed at opposite sides of a light propagating region, respectively.

When laser light polarized to a direction parallel to the Z axis, that is, a horizontal direction, is made to enter the waveguide in FIG. 1A and is propagated along the X axis, a terahertz wave is generated from the crystal surface on the basis of the principle discussed in NPL 2 of the related art or by optical rectification using an ultra-short pulse light source. The terahertz wave can be extracted to the surrounding space via the optical coupling member 7. A Cerenkov radiation angle determined by a light/terahertz-wave refractive-index difference in LN is about 65 degrees. In the case of the optical coupling member 7, i.e., prism, high-resistance Si with a small loss of terahertz wave, for example, is suitably used as a prism material that allows for extraction of the terahertz wave into the atmosphere without the terahertz wave undergoing total internal reflection in the waveguide. In this case, an angle θclad (see FIG. 1B) formed between the terahertz wave and the substrate surface is about 49 degrees. By making two beams of laser light having different frequencies enter the waveguide, as discussed in PTL 1 and NPL 2, a monochromatic terahertz wave is generated by a difference frequency generation (DFG) method. On the other hand, by making a single beam of laser light (pulse laser light) from a single ultra-short pulse light source (pulse laser light source) enter the waveguide, a short-pulse terahertz wave can be generated. In order to make the pulse laser light enter the waveguide, the pulse laser light may be simply condensed by a condenser optical system that uses an optical element, such as a lens, and be coupled to the waveguide, without requiring a wavefront tilt as in NPL 1. A thickness condition of the waveguide not requiring a wavefront tilt will be described later.

As mentioned above, in this embodiment, voltage can be applied via the electrodes 6a and 6b in the Z-axis direction corresponding to a pyro-axis direction of LN, that is, a direction corresponding to a maximum electro-optic constant, and the phase of the terahertz wave can be efficiently modulated by modulating the refractive index of the waveguide layer 4 by voltage modulation. Although the angle θclad in the output direction of the terahertz wave can possibly change due to the change in the refractive index, since this change in the refractive index is generally 0.1% or lower, the change does not have a dominant effect on signal information to be obtained from the terahertz wave. If a terahertz pulse is to be generated by femtosecond laser light irradiation, the pulse-time position can be modulated. The electrodes 6 each have, for example, a multilayer Ti/Au structure and may be formed directly on the LN surface, or may formed on a spacer layer (not shown) composed of $SiO_2$. However, the electrodes 6 are not directly in contact with the optical coupling member 7 and are configured so as not to come into electrical contact therewith. In order to achieve this, the thickness of the electrodes 6 or the electrodes 6 and the spacer layer is set to be 1 μm or smaller, and the thickness of the low-refractive-index buffer layer 5 for forming the waveguide is set to be about 3 μm. Specifically, this is achieved by positionally setting the bottom surface of the optical coupling member 7 to be higher than the electrodes 6 so as to form a gap. Accordingly, the voltage between the two electrodes 6a and 6b is efficiently applied mainly to the waveguide. The low-refractive-index buffer layer 5 has a thickness sufficient to function as a cladding layer when the laser light propagates through the waveguide layer 4, but is preferably thin to an extent that the effect of multiple reflection and loss is negligible when the terahertz wave is released to the outside via the optical coupling member 7. Regarding the former, in the waveguide in which the waveguide layer 4 as a high-refractive-index layer serves as a core layer whereas the adhesive 2 and the low-refractive-index buffer layer 5 as low-refractive-index layers serve as cladding layers, the aforementioned thickness is preferably greater than or equal to a thickness at which the light intensity at an interface between the low-refractive-index buffer layer 5 and the optical coupling member 7 is lower than or equal to $1/e^2$ of the light intensity of a core region. It should be noted that e is the base of natural logarithm. Regarding the latter, the thickness is preferably smaller than or equal to about 1/10 of an equivalent wavelength $\lambda_{eq}$ (THz), in the low-refractive-index buffer layer 5, of the terahertz wave at the maximum frequency to be released to the outside. This is because, in a structural body with a size corresponding to 1/10 of a wavelength, the effects of reflection, dispersion, refraction, and the like on the electromagnetic wave with that wavelength are generally considered to be negligible. It should be noted, however, that terahertz-wave generation from the terahertz-wave generating element according to the present invention is possible outside the aforementioned preferred thickness range.

By setting the configuration of the waveguide, the axial direction of the electro-optic crystal, and the configuration of the electrodes 6 in this manner, a terahertz wave can be generated by Cerenkov radiation, and the generated terahertz wave can be efficiently modulated. Specifically, a generating element that includes an electrical modulating unit (electrodes) provided for efficiently generating a high-intensity terahertz wave by photoexcitation and for detecting the generated terahertz wave at a high S/N ratio can be provided.

Figure 2A:
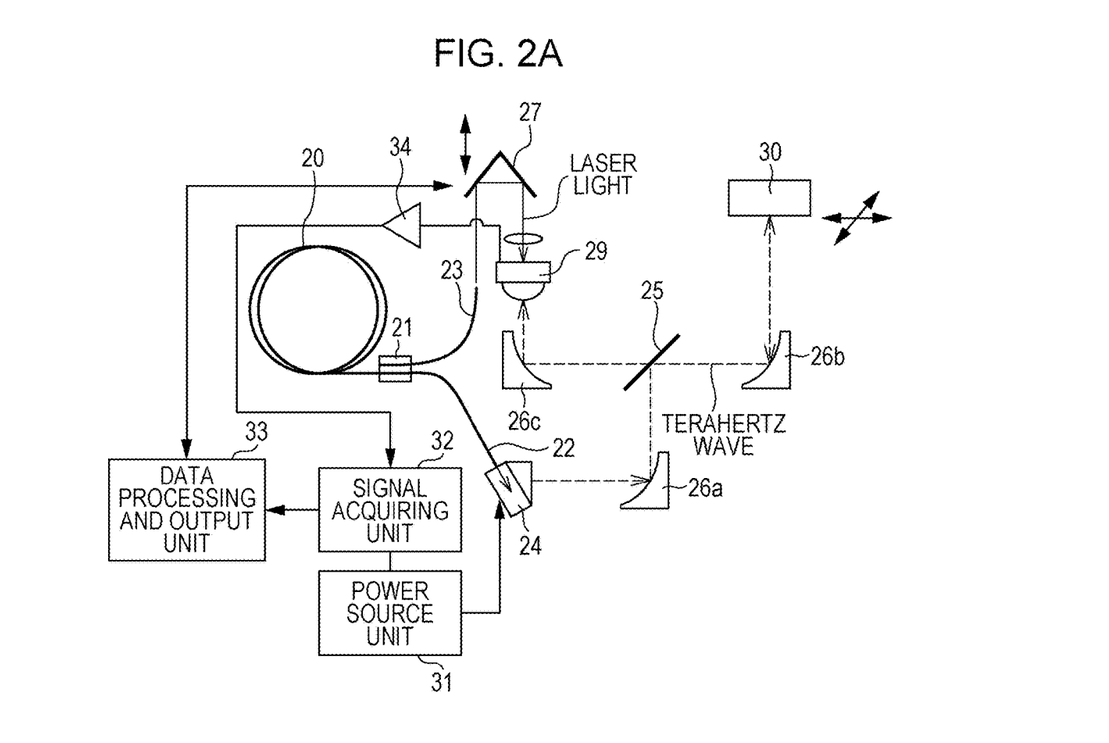
FIG. 2A is a configuration diagram of a tomography device according to an embodiment of the present invention.

FIG. 2A illustrates an example of a tomographic imaging device based on a terahertz time-domain spectroscopy system (THz-TDS) that uses the aforementioned element as a terahertz-wave generating element. In this case, a femtosecond laser 20 including optical fibers is used as an excitation light source, and an output is extracted from a fiber 22 and a fiber 23 via a demultiplexer 21. Although the femtosecond laser 20 used normally has a center wavelength of 1.55 μm, a pulse width of 20 fs, and a cyclic frequency of 50 MHz, the wavelength may alternatively be in a 1.06-μm band, and the pulse width and the cyclic frequency are not limited to the aforementioned values. Furthermore, the fibers 22 and 23 at the output stage may each include a high nonlinear fiber for high-order soliton compression at the final stage or a dispersive fiber that performs prechirping for compensating for dispersion by an optical element or the like extending to a terahertz generator and a terahertz detector. These fibers are preferably polarization-maintaining fibers.

The output from the fiber 22 at the terahertz-wave generating side is coupled to a waveguide of a Cerenkov-type phase-matching element 24 according to the present invention. In this case, it is preferable that the coupling efficiency be increased by integrating a Selfoc lens with the end of the fiber or by achieving a pigtail type by processing the aforementioned end so that the output is smaller than or equal to the numerical aperture of the waveguide of the element 24. It is needless to say that using a lens (not shown) to achieve spatial coupling is also permissible. In that case, the ends may each be provided with a nonreflective coating so as to reduce Fresnel loss and undesired interference noise. Alternatively, by designing the fiber 22 and the waveguide of the element 24 so that they have similar numerical apertures and similar mode field diameters, direct coupling (butt-coupling) by abutment is also permissible. In this case, an adhesive is appropriately selected so that an adverse effect caused by reflection can be reduced. If the fiber 22 or the femtosecond laser 20 at the preceding stage includes a non-polarization-maintaining fiber component, it is preferable to stabilize the polarization of input light entering the Cerenkov-radiation-type element 24 by using an inline-type polarization controller. However, the excitation light source is not limited to a fiber laser, and in that case, the countermeasure for stabilizing the polarization is reduced.

The generated terahertz wave is detected by the THz-TDS-based configuration shown in FIG. 2A. Specifically, the terahertz wave is made into a collimated beam by a parabolic mirror 26a and is split by a beam splitter 25. One of the split beams is irradiated onto a sample 30 via a parabolic mirror 26b. The terahertz wave reflected from the sample 30 is condensed by a parabolic mirror 26c and is received by a detector 29 defined by a photoconductor. The photoconductor used is normally a dipole antenna formed using low-temperature growth GaAs, and if the femtosecond laser 20 corresponds to 1.55 µm, a frequency-doubled wave is generated by using a SHG crystal (not shown) so as to provide probe light for the detector 29. In this case, in order to maintain the pulse shape, it is preferable to use PPLN (periodically poled lithium niobate) with a thickness of about 0.1 mm. If the femtosecond laser 20 corresponds to a 1-µm band, a fundamental wave can be used as the probe light in the detector 29 defined by the photoconductor constituted of an InGaAs single layer or a MQW, without generating a frequency-doubled wave. The device according to this embodiment is configured to perform synchronous detection by using a power source unit 31 that applies voltage to the waveguide of the element 24 and a signal acquiring unit 32 that acquires a detection signal from the detector 29 via an amplifier 34. A data processing and output unit 33 is configured to acquire a terahertz signal waveform while using a PC to move an optical delay unit 27 serving as a delay unit. The delay unit may be of any type so long as the delay unit is capable of adjusting a delay time between a time point at which the terahertz wave is generated by the element 24 serving as a generating unit (generator) and a time point at which the terahertz wave is detected by the detector 29 serving as a detecting unit (detector). As mentioned above, the aforementioned device includes the generating unit including the terahertz-wave generating element according to the present invention for generating a terahertz wave, the detecting unit for detecting the terahertz wave released from the generating unit, and the delay unit. This device functions as a tomography device that uses the detecting unit to detect the terahertz wave released from the generating unit and subsequently reflected by the sample and that acquires an image of the internal structure of the sample by analyzing the reflected light from the sample.

Figure 2B:
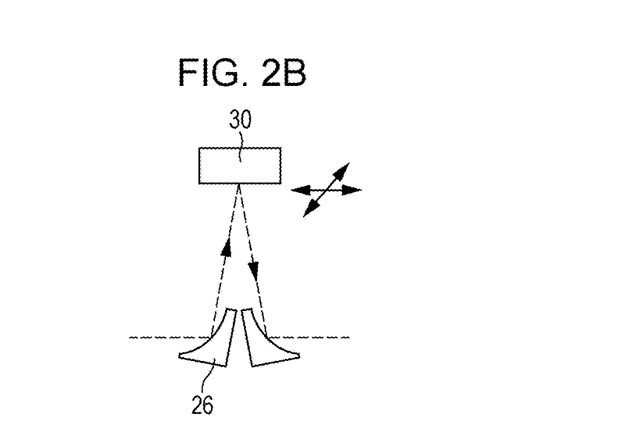
FIG. 2B is a configuration diagram of a modification of the tomography device according to the embodiment of the present invention.

In the system shown in FIG. 2A, the irradiated terahertz wave and the reflected wave from the sample 30 to be measured are coaxial with each other, and the power of the terahertz wave is reduced by half due to the presence of the beam splitter 25. Therefore, the irradiated terahertz wave and the reflected wave may be made non-coaxial with each other by increasing the number of mirrors 26, as in FIG. 2B, so as to increase the power of the terahertz wave, although the incident angle on the sample 30 in this case becomes unequal to 90 degrees.

If there is a discontinuous section in the material inside the sample 30, a signal to be acquired by using the aforementioned device would have a reflective echo pulse occurring at a time position corresponding to the discontinuous section. Thus, a tomographic image can be obtained by one-dimensionally scanning the sample 30, or a three-dimensional image can be obtained by two-dimensionally scanning the sample 30. Since the terahertz wave can be modulated with the terahertz-wave generating element 24 using a nonlinear optic crystal and provided with the electrodes 6 as mentioned above, the terahertz wave can be modulated in a frequency ranging from 50 kHz to 1 MHz, which is 10 times or more as compared with a case where the terahertz wave is modulated by using a mechanical component such as a light chopper. Thus, the synchronous detection frequency is improved, and the number of acquisitions of signal waveforms can be increased by scanning the optical delay unit 27 at high speed, thereby improving the S/N ratio. Consequently, finer signals can be detected, as compared with the related art, and the thickness of penetration in the sample 30 in the depth direction thereof can be increased in, for example, tomography. Furthermore, since a relatively narrow terahertz pulse of 300 fs or lower can be obtained with a mono-pulse, the depth resolution can be improved. Moreover, since an excitation laser using fibers can be used as an irradiating unit, the device can be reduced in size and cost.

Depending on the sample, there are cases where a reflection signal has high intensity and the S/N ratio is sufficient. In that case, an alternative modulating unit, such as a light chopper (not shown) as in the related art, may be used instead of performing the modulation using the electrodes 6. Even in that case, the tomography device can operate so as to generate a terahertz pulse of 300 fs or lower and to have high depth resolution, which is the characteristic feature of the present invention.

Although a LN crystal is used as the material here, other alternative examples of electro-optic crystals include LiTaOx, NbTaOx, KTP, DAST, ZnTe, GaSe, GaP, and CdTe, as mentioned in the background art. In this case, with LN, there is a refractive-index difference between the terahertz wave and the excitation light, as mentioned in the background art, so that a non-collinearly generated terahertz wave can be extracted. With other crystals, however, the difference is not always large, possibly making it difficult to extract the terahertz wave. However, by using a prism (such as a Si prism) having a refractive index greater than that of an electro-optic crystal, the condition of Cerenkov radiation ($V_{THz}$<vg) can be satisfied, whereby the terahertz wave can be extracted to the outside.

Practical Example 1

A detailed practical example 1 corresponding to the first embodiment will now be described. In the element structure shown in FIGS. 1A and 1B in this practical example, an optical adhesive layer 2 having a refractive index n of about 1.5 is formed to a thickness of 3 μm, and a MgO-doped waveguide layer 4 is formed to a thickness of 3.8 μm.

The thickness of the waveguide layer 4 is determined as follows. First, a maximum frequency fmax of a terahertz pulse (terahertz wave) to be obtained is determined from that terahertz pulse. The maximum frequency fmax corresponds to a maximum frequency when the terahertz pulse to be obtained is Fourier-transformed. Then, the thickness of the waveguide layer 4 is smaller than or equal to half the length of an equivalent wavelength (effective wavelength) within the electro-optic crystal, corresponding to the maximum frequency fmax of the terahertz wave extracted to the space, and a single mode condition corresponding to a good coupling efficiency and a low propagation loss of input pulse laser light is satisfied. In order to handle up to, for example, 7.5 THz in this practical example, the wavelength in a free space is about 40 μm, and if the refractive index of the terahertz wave in the LN waveguide layer is 5.2, the thickness of the waveguide layer is preferably $\lambda_{eq}(THz)/2$ (=40/5.2/2)≈3.8 μm. On the other hand, in view of the coupling efficiency and the propagation loss, the optical waveguide in this practical example preferably has a thickness of about 5 μm when the center wavelength of the input laser light is 1.55 μm (waveguide simulation result). However, the lower condition, that is, the thickness of 3.8 μm, is preferentially selected so as to ensure a terahertz wave band. In this case, fmax=7.5 THz in this practical example corresponds to a frequency of LO phonon absorption of the LN crystal and is set because the terahertz wave is significantly absorbed and not released near that frequency. There are cases where irradiation of, for example, 10 THz or higher, which is a frequency that is higher than the LO phonon absorption band, is possible depending on the pulse width of the input laser light. In that case, the thickness of the optical waveguide is reduced accordingly. Furthermore, if the center wavelength of the input laser light is 1 μm, an optimal thickness is about 3.6 μm based on simulation, and in this case, this thickness is selected. It is thus important to determine the thickness of the waveguide layer 4 in view of the differences in the required terahertz band or the condition of a good coupling efficiency and a low propagation loss of the input laser light, and it is preferable to select the lower one of these two conditions as an optimal mode.

On the other hand, a low-refractive-index buffer layer 5 with a width of 5 μm is formed to a thickness of 2 μm using the same optical adhesive as that used for the optical adhesive layer 2. Similarly, in order to handle up to 7.5 THz, assuming that the equivalent wavelength is equal to a value divided by the refractive index 1.5 of the low-refractive-index buffer layer 5, the thickness is set to 2 μm, which is smaller than or equal to $\lambda_{eq}/10$ (=40/1.5/10) 2.7 μm, as mentioned in the first embodiment.

Furthermore, an optical coupling member (prism) 7 formed of high resistance Si and having an angle θ of 50 degrees in FIG. 1B is attached. In this case, the angle θ and the radiation angle of the terahertz wave are substantially the same, and the terahertz wave exits the optical coupling member 7 substantially orthogonally from an inclined surface thereof. It should be noted, however, that the angle θ does not necessarily need to be equal to θclad, and that the terahertz wave does not necessarily need to exit orthogonally.

Driving conditions in this practical example will now be described. An electro-optic (EO) coefficient γ of LN is at maximum in the Z-axis direction and is about 30 μm/V, and a change Δn in refractive index due to the Pockels effect, which is a first-order electro-optic effect, is expressed as follows.

$$\Delta n \approx \tfrac{1}{2} \cdot n_0^3 \cdot \gamma \cdot E$$

In this case, $n_0$=2.2 (LN:MgO), and E denotes an applied electric field. When the voltage is changed in a rectangular manner within +/−30 V, Δn is about 0.002 if the waveguide has a width of 5 μm. When the length of the waveguide equipped with the electrodes 6 of the element is 10 mm, the refractive index changes by 1/1000, whereby the propagation distance of the propagating laser light appears as a difference of about 10 μm. This is equivalent to about 30 fs in terms of time difference, that is, about 10% of the pulse width 300 fs of an assumed terahertz pulse.

Figure 3A:
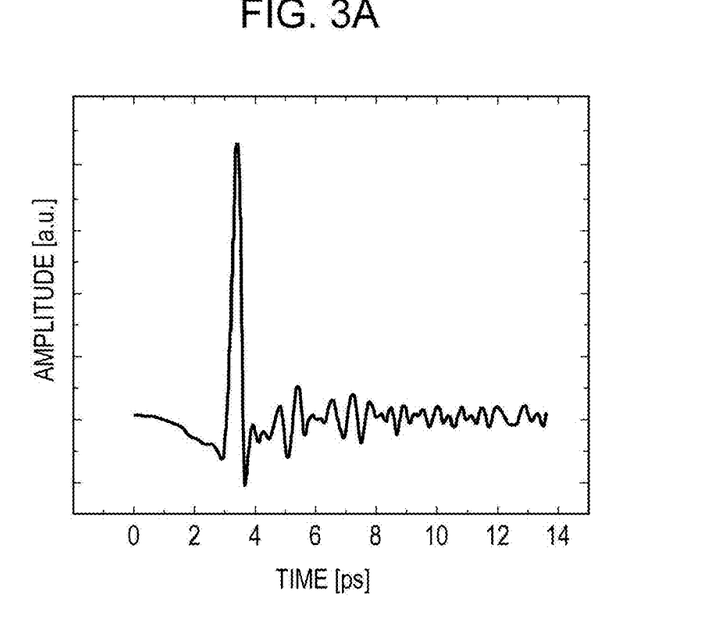
FIG. 3A illustrates an example of a terahertz pulse waveform irradiated onto a sample by the tomography device according to the embodiment of the present invention.
Figure 3B:
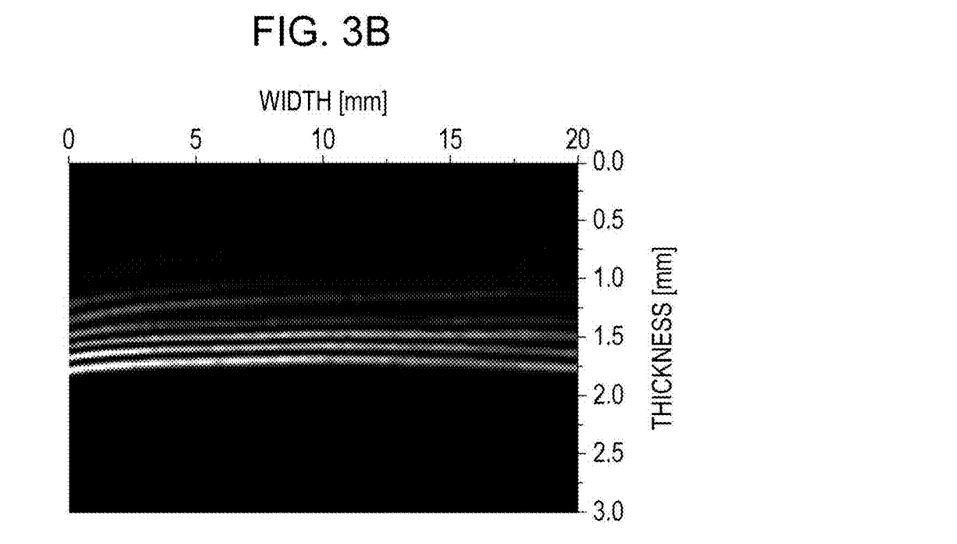
FIG. 3B illustrates an example of a tomographic image acquired by the tomography device according to the embodiment of the present invention.

By performing synchronous detection in a phase mode while performing phase modulation on such a terahertz pulse, a tomographic image of the sample 30 is acquired using the system shown in FIG. 2A. Although this is effective for peak-position detection, that is, tomographic-image acquisition so as to ascertain a slight difference in the phase mode, there is a large error in a spectral analysis, that is, in the acquisition of the entire waveform of the terahertz pulse. FIG. 3A illustrates an example of a waveform of a terahertz pulse irradiated onto a sample, and FIG. 3B illustrates an example of an acquired tomographic image. It is apparent from FIG. 3A that a mono-pulse with a pulse width of about 270 fs is obtained. The tomographic image shown in FIG. 3B is obtained by performing a unidirectional scan on a sample formed of three stacked paper sheets each having a thickness of about 90 μm. The reason that there appears to be six layers (white lines) is because the paper sheets have gaps formed of air therebetween, and that the front and rear faces of the paper sheets are considered as interfaces. It is needless to say that the phase difference may be further increased by further increasing the electrode length.

Second Embodiment

A second embodiment of the present invention will now be described with reference to FIG. 4. On a substrate 40 in this embodiment, a waveguide 42 through which laser light propagates is a sandwich-type slab waveguide, and voltage-applying electrodes 45 (45a and 45b) are orthogonal to the light propagating direction. The laser-light propagating direction and the electric-field application direction are aligned with each other. This embodiment corresponds to Y-cut and Z-axis-propagating direction, and the X axis is aligned with the polarization direction of input laser light.

Figure 4:
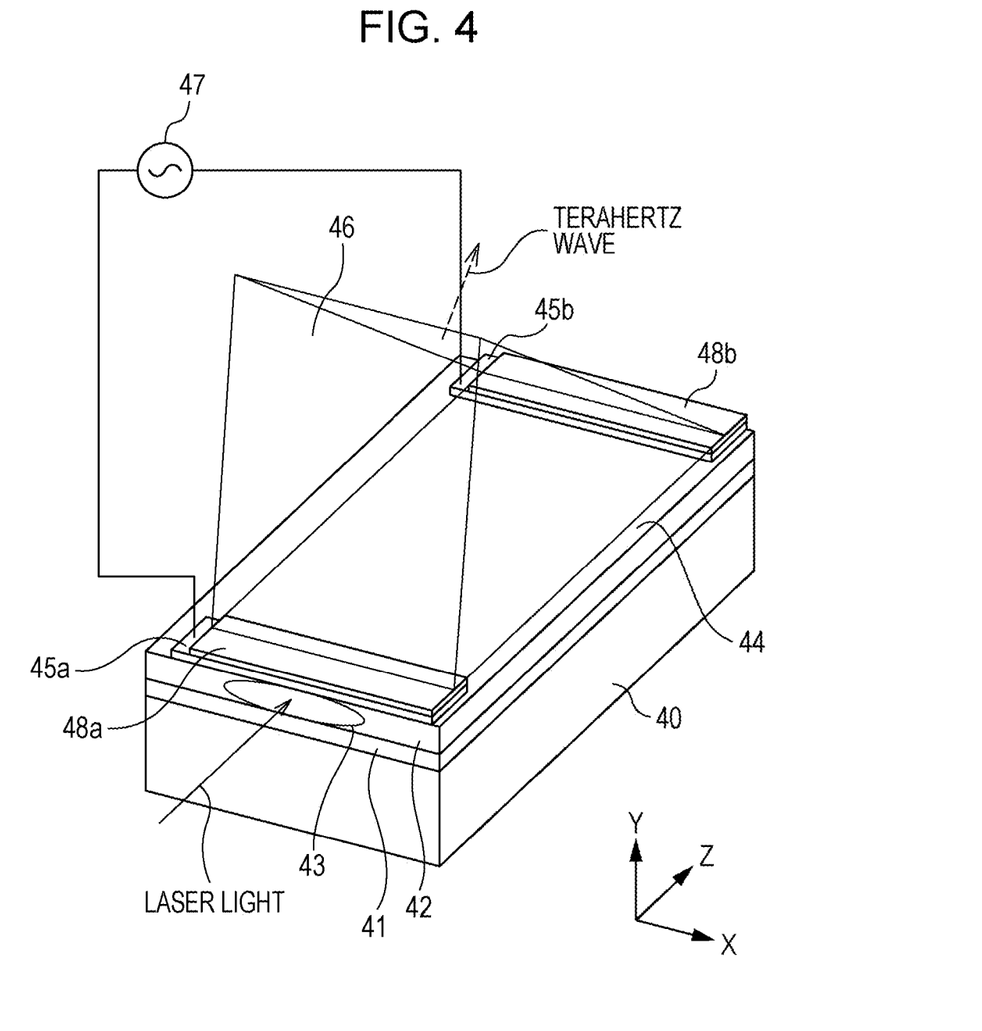
FIG. 4 is a structural view of a terahertz-wave generating element according to a second embodiment of the present invention.

In the structure in FIG. 4, reference numeral 41 denotes an adhesive layer similar to that in the first embodiment. The waveguide length is, for example, 5 mm. The electrodes 45a and 45b are disposed at the input side and the terminal side, respectively, as shown in FIG. 4, and receive voltage from a power source 47 so as to modulate a generated terahertz wave. An optical coupling member 46 is bonded to the surfaces of the electrodes 45 by forming insulating films 48a and 48b composed of SiO$_2$ or the like thereon so as not to be in direct contact with the electrodes 45. In this case, the optical coupling member 46 can be fixed to the two insulating films 48a and 48b in a bridge-like manner so that a gap 44 is formed between the waveguide 42 and the optical coupling member 46. Therefore, the laser light can propagate through the waveguide 42 without a low-refractive-index buffer layer as in the first embodiment.

The input light may be in the shape of an oval, as denoted by a reference numeral 43. In this case, a rod lens may be used as a lens for coupling the light from the laser light source so that the light is throttled only in the vertical direction of the layered structure of the waveguide 42. In order to handle a wide input beam entering the slab waveguide 42 in this embodiment, the electrodes 45 are disposed as in FIG. 4 instead of along the waveguide 42. Although the modulation voltage in this embodiment is higher than that in the first embodiment, a spatial region where a terahertz wave is generated can be increased in size.

Third Embodiment

Figure 5:
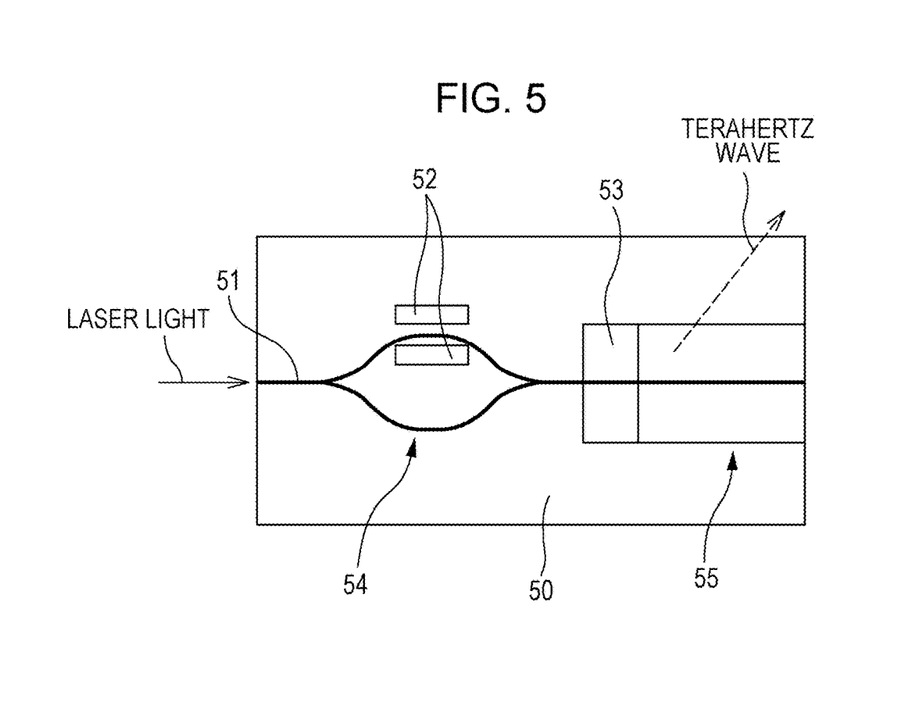
FIG. 5 is a structural view of a terahertz-wave generating element according to a third embodiment of the present invention.

As shown in FIG. 5 in plan view, a third embodiment according to the present invention provides an integrated element having a first stage provided with a Mach-Zehnder-interferometer-type intensity modulator 54 including two Y-branch sections, i.e., a Y demultiplexer and a Y multiplexer, and a second stage provided with a terahertz-wave generator 55. The material used here can be a nonlinear optic crystal 50 mainly composed of LN as in the above embodiments. The Mach-Zehnder-interferometer-type intensity modulator 54 is provided with two electrodes 52 and is capable of modulating the intensity of propagating light.

The first stage is a generally known modulator that splits input laser light 51 into two components by using a Y-branch waveguide. By applying a voltage $V_\pi$ (i.e., a voltage that generates a phase difference n between the two Y-branch sections) to the electrodes 52, the refractive index of the nonlinear optic crystal 50 having an effect on the propagation state of the propagating light is changed so as to change the phases, as in the first embodiment, thereby performing adjustment such that the phases are inverted relative to each other at the multiplexing point. When the applied voltage is equal to $V_\pi$, the laser light beams cancel each other out, causing the laser light propagating through the terahertz-wave generator 55 to vanish. On the other hand, when the applied voltage is equal to zero or smaller than $V_\pi$, the laser light components are multiplexed at the Y multiplexer, causing excitation laser light to enter the terahertz-wave generator 55. Thus, a terahertz wave is emitted upward by an optical coupling member 53. In this manner, a terahertz wave is generated from the intensity-modulated light propagating through the waveguide. In this embodiment, the intensity of the terahertz wave is modulated so as to readily allow for synchronization in an amplitude mode when performing synchronous detection.

Fourth Embodiment

The description above is directed to an example in which a terahertz pulse is generated by optical rectification using femtosecond laser light as excitation light. In contrast, in the fourth embodiment, laser light beams having two different oscillation frequencies ν1 and ν2 are input, and a monochromatic terahertz wave corresponding to a difference in the frequencies is output. As a laser light source, a KTP-OPO (optical parametric oscillator) light source of Nd:YAG laser excitation (which outputs light of two wavelengths) or two wavelength tunable laser diodes may be used.

Figure 6:
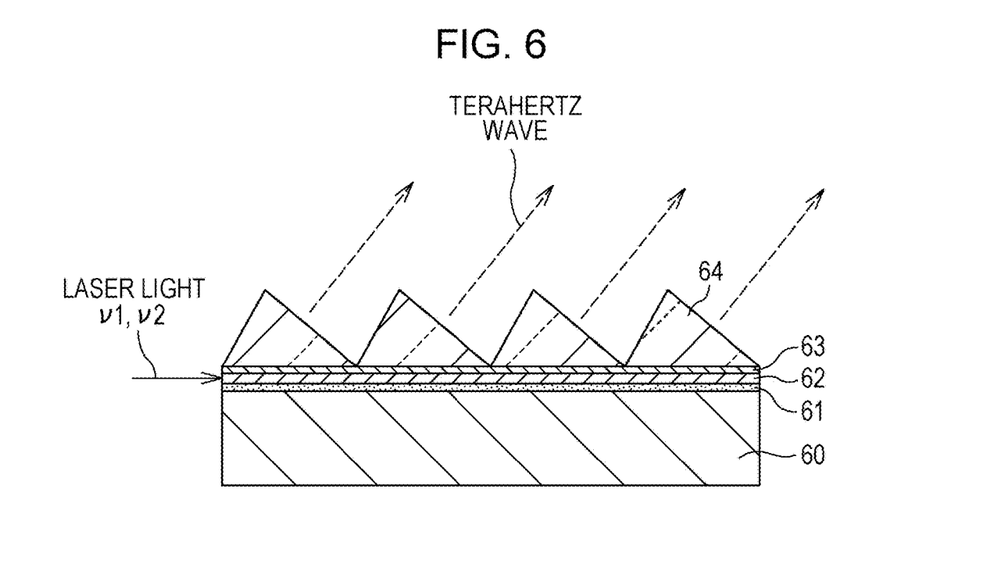
FIG. 6 is a structural view of a terahertz-wave generating element according to a fourth embodiment of the present invention.

FIG. 6 is a cross-sectional view corresponding to this embodiment. An adhesive layer 61, a MgO-doped LN waveguide layer 62, and a low-refractive-index buffer layer 63 are stacked on a LN substrate 60. Similar to the first embodiment, a 5-μm-width waveguide and electrodes for voltage application on opposite sides thereof are also formed, although not shown. In order to increase the output of a terahertz wave in this embodiment, the waveguide length is 40 mm, and multiple optical coupling members 64 are provided. Four optical coupling members 64, each with a length of, for example, about 1 cm, are arranged as shown in FIG. 6. By forming an optical coupling unit with the multiple optical coupling members 64, the entire volume thereof can be reduced, thereby reducing the length by which the terahertz wave travels through the optical coupling unit and thus allowing for reduced loss.

In this embodiment, when the frequency difference of input light is changed from 0.5 THz to 7 THz, the frequency of the released terahertz wave can be varied within that range. This embodiment can be applied to an inspection or imaging using a frequency of a specific terahertz band, for example, an inspection by checking the content of a specific material in a medicinal drug by adjusting the frequency to the absorption spectrum of that material.

Fifth Embodiment

Figure 7:
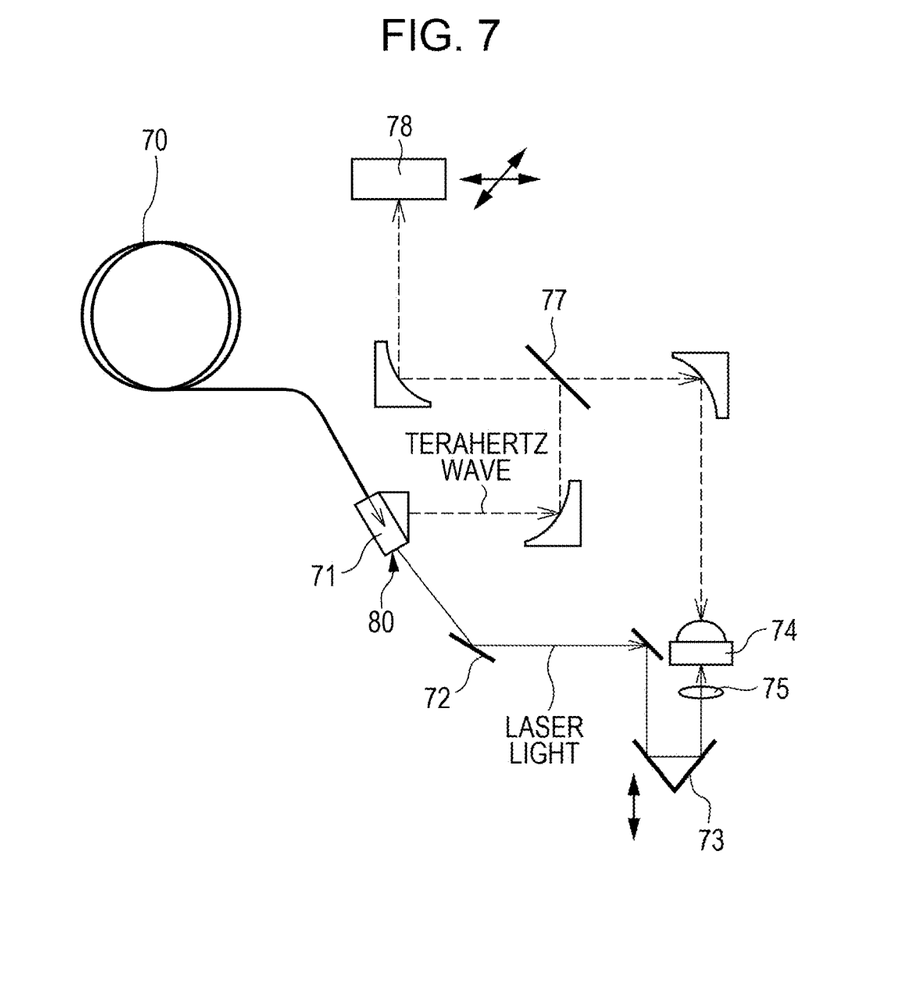
FIG. 7 is a configuration diagram of a tomography device according to another embodiment of the present invention.

In the embodiments and the practical example described above, a terminal end 80 of a waveguide of a terahertz-wave generating element 71 using LN, as in FIG. 7, is roughened, is diagonally cut to extract the light to the outside, or is given an AR coating so that the light exiting the terminal end 80 is prevented from becoming a source of noise. In contrast, in the fifth embodiment, the terminal end 80 is diagonally cut or is given an AR coating so as to reutilize the light exiting the terminal end 80 as probe light. Specifically, in this embodiment, the light from the terminal end 80 of the waveguide of the terahertz-wave generating element 71 is utilized as probe light for a detecting unit, and a delay unit adjusts the delay time between the arrival time of the light at the waveguide of the terahertz-wave generating element 71 and the arrival time of the probe light at the detecting unit.

FIG. 7 illustrates a THz-TDS-type tomography device similar to that shown in FIG. 2A. In FIG. 7, an electric system is not shown. This embodiment differs from that shown in FIGS. 2A and 2B in that a fiber branch section is not provided, and an output from an excitation laser 70 including a fiber is entirely input to the terahertz-wave generating element 71. A terahertz wave generated from the terahertz-wave generating element 71 is irradiated onto a sample 78 via parabolic mirrors and a half mirror 77, as in the embodiment shown in FIGS. 2A and 2B. Reflected light from the sample 78 enters a terahertz detector 74 where signal acquisition is performed. On the other hand, a portion of the laser light propagating through the terahertz-wave generating element 71 is re-output from the terminal end 80 so as to be utilized as probe light of the detector 74 via a mirror 72, a delay unit 73, and a lens 75.

Since this configuration does not require a branch section for the excitation laser light, the number of components can be reduced, and the power of the excitation laser 70 can be efficiently utilized.

Sixth Embodiment

Figure 9:
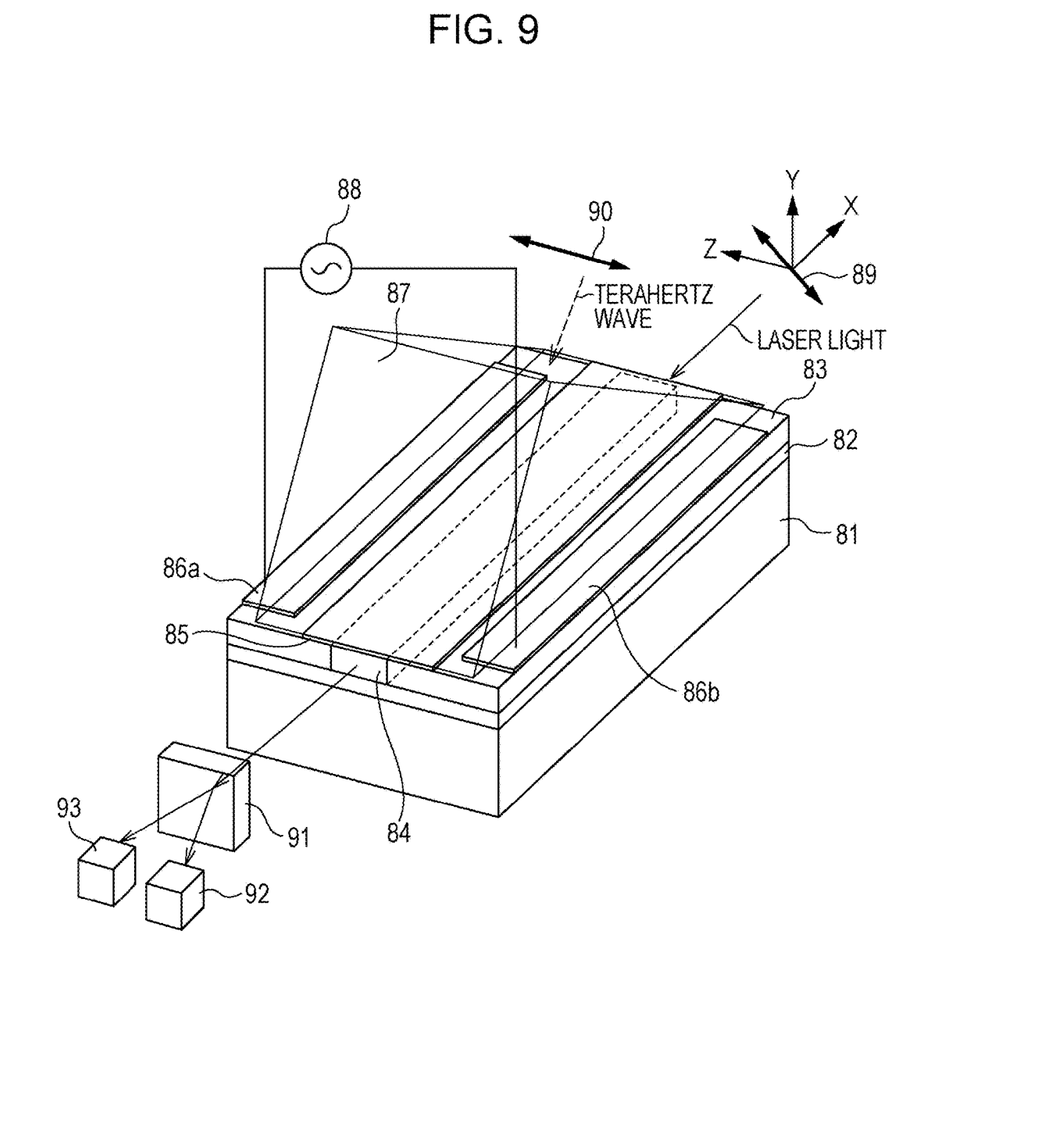
FIG. 9 is a structural view of a terahertz-wave detecting element according to an embodiment of the present invention.

In this embodiment, an element having the same structure as the above-described element is used to function as a terahertz-wave detecting element. Specifically, as shown in FIG. 9, on a LN substrate 81, an adhesive 82, a waveguide layer 84 formed of a MgO-doped LN crystal layer, and a low-refractive-index buffer layer 85 form a waveguide that propagates input laser light by total internal reflection.

Moreover, electrodes 86a and 86b and an optical coupling member 87 are further provided so that a terahertz wave can be output by Cerenkov radiation. In this embodiment, ultrashort pulse laser light is input from a side opposite to that in the above embodiments while a polarized wave 89 is inclined (for example, by 45 degrees) from the Z axis of the crystal by linear polarization. Regarding the output laser light in this case, a phase difference occurs between a Z-axis component and a Y-axis component of an electric field due to birefringence of the electro-optic crystal, causing the light to propagate as an elliptically polarized wave through a space to which the light is output. The phase difference occurring due to such natural birefringence varies depending on the type of crystal, the direction of input polarized wave, or the waveguide length, and a configuration for zero phase difference is also possible. By statically adjusting this phase difference using an electrostatic field applied to the electrodes 86a and 86b, the phase difference can be adjusted to zero when the terahertz electric field is zero.

When a terahertz pulse whose main axis of a polarized wave is the Z axis is input via an optical coupling member, e.g., a Si prism 87, a reverse process of terahertz wave generation causes an interaction to occur between the terahertz wave and the ultra-short pulse laser light propagating through the waveguide over the entire waveguide. The term "interaction" refers to a change in the polarization state of the propagating light owing to a change in the refractive index of the waveguide on the Z axis due to a first-order electro-optic effect (Pockels effect, second-order nonlinear process) imparted on the electro-optic crystal by a terahertz electromagnetic field. Specifically, the phase difference between the Z-axis component and the Y-axis component of the electric field of the laser light changes due to induced birefringence, causing the ellipticity of the elliptically polarized wave and the direction of the main axis to change.

By detecting the change in the propagation state of the laser light by using external components, such as a polarizing element 91 and light detectors 92 and 93, the magnitude of the electric-field amplitude of the terahertz wave can be detected. In this embodiment, the natural birefringence is compensated by the electrostatic field applied to the electrodes 86a and 86b, as mentioned above, and the polarizing element (Wollaston polarizing prism, etc.) 91 is used to separate the light into two polarized light components so that the S/N ratio is improved by differential amplification of the two light detectors 92 and 93. The differential amplification is not mandatory, and the intensity may be detected with only a single light detector while using the polarizing element 91 as a polarizer, although this configuration is not shown.

In order to stabilize the compensation of the natural birefringence, a low frequency sine-wave signal may be superimposed on the voltage applied to the electrodes 86a and 86b so as to suppress offset fluctuations by a known wobbling technique. Furthermore, the compensation is sometimes not possible with the applied voltage alone depending on the waveguide length. In that case, a phase compensating plate (such as a quarter-wave plate, not shown) may be additionally provided between the output end and the polarizing element 91.

Furthermore, a terahertz detection signal itself can be modulated by performing the modulation using the electrodes so as to perform synchronous detection. Moreover, by performing frequency separation into synchronous detection frequency and wobbling modulation frequency, both control operations can be performed simultaneously. For example, this synchronous detection frequency may be set to be 1 MHz and the wobbling modulation frequency may be set to be 1 kHz.

By performing such synchronous detection, the terahertz time-domain spectroscopy device and the tomography device described in the above embodiments can be achieved. In this case, the generating element may either be of a Cerenkov phase-matching type as in the present invention or a type that uses a photoconductor as in the related art.

Although the light is input from the end opposite to the terahertz-wave generated side in this embodiment, the light may alternatively be input from the same side as the terahertz-wave generated side. In that case, the signal strength becomes smaller since the matching length is reduced.

Although the optical waveguide has a ridge pattern as in the first embodiment, a slab waveguide is also permissible, as in the second embodiment.

Although the description above is directed to an example in which a terahertz pulse is detected using pulse laser light, two beams of laser light having two different frequencies may be input, as in the fourth embodiment, so that a monochromatic terahertz wave corresponding to a difference frequency component thereof can be detected. In that case, by changing the difference in frequencies, a terahertz wave of a desired frequency can be extracted like a filter so as to detect the electric-field amplitude.

As a method of detecting a terahertz wave, a method of detecting a change in the polarization state of light in accordance with a first-order electro-optic effect by a coupled terahertz wave is described above. An alternative method includes detecting a beat signal of light, that is, detecting a light signal corresponding to a difference between the frequency of light propagating through the waveguide and the frequency of the coupled terahertz wave, or detecting a change in the phase of light propagating through the waveguide as a change in the propagation state of the light.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

It should be noted that the technical elements described in the specification and/or illustrated in the drawings provide technical utility individually or by any suitable combination thereof, and should not be limited to the combinations discussed in the claims at the time of the application. Furthermore, the technology described in the specification and/or illustrated in the drawings can simultaneously achieve multiple objects, and can have technical utility by simply achieving at least one of the objects.

Industrial Applicability

As described above, the present invention can be applied to a terahertz-wave generating element, a terahertz-wave detecting element, a terahertz time-domain spectroscopy device, and a tomography device.

The invention claimed is:
1. A terahertz-wave generating element, comprising:
a substrate;
a waveguide arranged on the substrate and configured to propagate light in a first direction; and an optical coupling member arranged on the waveguide and guiding a terahertz wave, which is generated due to light propagating through the waveguide, from the waveguide to a space, wherein the waveguide is formed of a material selected from a group consisting of LiNbOx, LiTaOx, NbTaOx, KTP, DAST, ZnTe, GaSe, GaP, and CdTe, and wherein in a third direction perpendicular to the first direction and perpendicular to a second direction perpendicular to an in-plane direction of the substrate, a width of the waveguide is smaller than a width of the optical coupling member.

2. The terahertz-wave generating element according to claim 1, wherein a thickness of the waveguide is equal to or smaller than a half of an equivalent wavelength of the terahertz wave in the waveguide.

3. The terahertz-wave generating element according to claim 1, wherein a low-refractive-index layer has a refractive index lower than a refractive index of the waveguide, wherein the low-refractive-index layer is disposed between the optical coupling member and the waveguide, and wherein a thickness d of the low-refractive-index layer satisfies $a<d<\lambda_{eq}/10$, where a denotes a thickness corresponding to a light intensity $1/e^2$ of the light in the waveguide, and $\lambda_{eq}$ denotes the equivalent wavelength of the terahertz wave in the low-refractive-index layer.

4. The terahertz-wave generating element according to claim 1, wherein the waveguide is a waveguide having a ridge pattern.

5. A terahertz time-domain spectroscopy device comprising:

a generator that generates a terahertz wave; and
a detector that detects the terahertz wave,
wherein the generator includes the terahertz-wave generating element according to claim 1.

6. The terahertz-wave generating element according to claim 1, wherein a material of the optical coupling member is silicon.

7. The terahertz-wave generating element according to claim 1, wherein a wavelength of the light is shorter than a wavelength of the terahertz wave.

8. The terahertz-wave generating element according to claim 7, wherein in the third direction, the width of the waveguide is smaller than the wavelength of the terahertz wave.

9. The terahertz-wave generating element according to claim 1, wherein the waveguide is formed of LiNbOx.

10. The terahertz-wave generating element according to claim 9, wherein a height of an apex of the optical coupling member in a cross-section in the first direction monotonically decreases down to an end of the substrate on a side from which the light exits.

11. The terahertz-wave generating element according to claim 10, wherein a first side-surface of the optical coupling member and a second side surface of the optical coupling member form the apex of the optical coupling member, wherein the second side surface is the surface from which the terahertz wave exits; and wherein an angle formed by the first side surface of the optical coupling member and a main surface of the substrate is greater than an angle formed by the second side surface of the optical coupling member and the main surface of the substrate.

12. The terahertz-wave generating element according to claim 1, wherein the waveguide is disposed between members having a refractive index lower than a refractive index of the waveguide in the third direction.

13. The terahertz-wave generating element according to claim 1, wherein a length of the optical coupling member in the second direction gradually becomes shorter in a direction in which light is propagated through the waveguide.

14. The terahertz-wave generating element according to claim 1, wherein the optical coupling member and the waveguide extend in the first direction.

15. The terahertz-wave generating element according to claim 1, further comprising: an optical fiber, wherein the optical fiber is arranged to be coupled to the waveguide.

16. The terahertz-wave generating element according to claim 15, wherein the optical fiber is a polarization-maintaining fiber.

17. A terahertz-wave generating element comprising:

a substrate;
a waveguide arranged on the substrate and configured to propagate light in a first direction; and
a member arranged on the waveguide,
wherein a length of the member in a second direction perpendicular to an in-plane direction of the substrate gradually becomes shorter in the first direction, and
wherein, in a third direction perpendicular to the first direction and perpendicular to the second direction, a width of the member is larger than a width of the waveguide.

18. The terahertz-wave generating element according to claim 17, wherein the waveguide is formed of a material selected from a group consisting of LiNbOx, LiTaOx, NbTaOx, KTP, DAST, ZnTe, GaSe, GaP, and CdTe.

19. The terahertz-wave generating element according to claim 17, wherein the waveguide is formed of LiNbOx.

20. The terahertz-wave generating element according to claim 19, wherein a height of an apex of the optical coupling member in a cross-section in the first direction monotonically decreases down to an end of the substrate on a side from which the light exits.

21. The terahertz-wave generating element according to claim 20, wherein a first side surface of the optical coupling member and a second side surface of the optical coupling member form the apex of the optical coupling member, wherein the second side surface is the surface from which the terahertz wave exits; and wherein an angle formed by the first side surface of the optical coupling member and a main surface of the substrate is greater than an angle formed by the second side surface of the optical coupling member and the main surface of the substrate.

22. The terahertz-wave generating element according to claim 17, wherein the waveguide is disposed between regions having a refractive index lower than a refractive index of the waveguide in the third direction.

23. The terahertz-wave generating element according to claim 17, wherein the member is formed of silicon.

24. The terahertz-wave generating element according to claim 17, wherein the waveguide and the member extend in the first direction.

25. The terahertz-wave generating element according to claim 14, further comprising:

an optical fiber, wherein the optical fiber is arranged to be coupled to the waveguide.

26. The terahertz-wave generating element according to claim 25, wherein the optical fiber is a polarization-maintaining fiber.

27. A terahertz time-domain spectroscopy device comprising:
a generation unit configured to generate a terahertz wave; and
a detection unit configured to detect the terahertz wave, wherein the generation unit includes the terahertz-wave generating element according to claim 17.

28. A terahertz-wave generating element comprising:
a substrate;
a waveguide arranged on the substrate and configured to propagate light in a first direction;
a member arranged on the waveguide; and
an optical fiber configured to guide light to the waveguide,
wherein the member is formed of silicon,
wherein a length of the member in a second direction perpendicular to an in-plane direction of the substrate gradually becomes shorter in a first direction, and
wherein, in a third direction perpendicular to the first direction and perpendicular to the second direction, a width of the member is larger than a width of the waveguide.

29. The terahertz-wave generating element according to claim 28, wherein the waveguide is formed of a material selected from a group consisting of LiNbOx, LiTaOx, NbTaOx, KTP, DAST, ZnTe, GaSe, GaP, and CdTe.

30. The terahertz-wave generating element according to claim 28, wherein the waveguide is formed of LiNbOx.

31. The terahertz-wave generating element according to claim 28, wherein the waveguide is disposed between regions having a refractive index lower than a refractive index of the waveguide in the third direction.

32. The terahertz-wave generating element according to claim 28, wherein the waveguide and the member extend in the first direction.

33. The terahertz-wave generating element according to claim 28, weherein terahertz waves emitted from the member are phase-matched.

34. A terahertz time-domain spectroscopy device comprising:
a generation unit configured to generate a terahertz wave; and
a detection unit configured to detect the terahertz wave, wherein the generation unit includes the terahertz-wave generating element according to claim 28.

35. The terahertz-wave generating element according to claim 28, wherein a height of an apex of the optical coupling member in a cross-section in the first direction monotonically decreases down to an end of the substrate on a side from which the light exits.

36. The terahertz-wave generating element according to claim 35,
wherein a first side surface of the optical coupling member and a second side surface of the optical coupling member form the apex of the optical coupling member,
wherein the second side surface is the surface from which the terahertz wave exits; and
wherein an angle formed by the first side surface of the optical coupling member and a main surface of the substrate is greater than an angle formed by the second side surface of the optical coupling member and the main surface of the substrate.

37. The terahertz-wave generating element according to claim 28, wherein the optical fiber is a polarization-maintaining fiber.

38. The terahertz-wave generating element according to claim 37, wherein the waveguide is formed of LiNbOx.

39. The terahertz-wave generating element according to claim 38, wherein a height of an apex of the optical coupling member in a cross-section in the first direction monotonically decreases down to an end of the substrate on a side from which the light exits.

40. The terahertz-wave generating element according to claim 39, wherein terahertz waves emitted from the member are phase-matched.

41. The terahertz-wave generating element according to claim 39,
wherein a first side surface of the optical coupling member and a second side surface of the optical coupling member form the apex of the optical coupling member,
wherein the second side surface is the surface from which the terahertz wave exits; and
wherein an angle formed by the first side surface of the optical coupling member and a main surface of the substrate is greater than an angle formed by the second-side surface of the optical coupling member and the main surface of the substrate.

* * * * *